United States Patent
Schroeder et al.

(10) Patent No.: US 7,119,224 B2
(45) Date of Patent: Oct. 10, 2006

(54) PREPARATION OF (METH) ACRYLIC ACID AND (METH) ACRYLIC ESTERS

(75) Inventors: Juergen Schroeder, Ludwigshafen (DE); Frank Hoefer, Ludwigshafen (DE); Sylke Haremza, Neckargemuend (DE); Gerhard Wagenblast, Wachenheim (DE); Volker Schliephake, Schifferstadt (DE); Ulrich Jaeger, Roemerberg (DE); Harald Keller, Ludwigshafen (DE); Cedric Dieleman, Scheibenhard (FR)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/651,966

(22) Filed: Sep. 2, 2003

(65) Prior Publication Data

US 2005/0261523 A1    Nov. 24, 2005

(30) Foreign Application Priority Data

Oct. 17, 2002   (DE)  ................................. 102 48 606

(51) Int. Cl.
*C07C 51/42*    (2006.01)
*C07C 67/48*    (2006.01)
*C07C 69/52*    (2006.01)
*C07C 69/54*    (2006.01)

(52) U.S. Cl. ....................... 560/205; 560/218; 562/600; 203/8

(58) Field of Classification Search .................... 203/8, 203/49, 98, DIG. 21, DIG. 25; 562/600; 560/205, 218
See application file for complete search history.

(56) References Cited

U.S. PATENT DOCUMENTS 4,263,448 A * 4/1981 Leacock ...................... 560/246

FOREIGN PATENT DOCUMENTS

EP    1 035 102    9/2000

* cited by examiner

*Primary Examiner*—Taylor Victor Oh
(74) *Attorney, Agent, or Firm*—Oblon, Spivak, McClelland, Maier & Neustadt, P.C.

(57) ABSTRACT

A process for preparing and/or working up mixtures by (meth)acrylic acid and/or (meth)acrylic ester in the presence of at least one polymerization inhibitor and at least one oxygenous gas, which comprises metering in at least part of the oxygenous gas at an exit rate of at least 50 mm/s.

19 Claims, 2 Drawing Sheets

PREPARATION OF (METH) ACRYLIC ACID AND (METH) ACRYLIC ESTERS

The present invention relates to a process for reducing the polymerization in the preparation of (meth)acrylic acid and (meth)acrylic esters.

It is known that polymerizable compounds such as (meth) acrylic acid and (meth)acrylic ester can easily be induced to polymerize, for instance by heat or by the action of light or peroxides. However, since polymerization has to be reduced or prevented for safety and economic reasons in the preparation, workup and/or storage, there is a constant need for novel, simple and effective methods for reducing the polymerization.

It is well-known prior art that the polymerization of (meth)acrylic acid and (meth)acrylic esters can be suppressed by using polymerization inhibitors, frequently in combination with oxygenous gases.

In the case of distillation columns or in the case of reactors, these oxygenous gases are generally metered into the bottom, for example into the bottom circuit.

EP-A 1 035 102 describes a process for purifying (meth) acrylic acid and (meth)acrylic esters by metering an oxygenous gas into the circuit of the evaporator.

These processes in which oxygenous gases are metered into the bottom of a distillation column or of a reactor have the disadvantage that they do not prevent the polymerization of (meth)acrylic acid and (meth)acrylic ester effectively enough.

BRIEF DESCRIPTION

It is an object of the present invention to provide a process for preparing (meth)acrylic acid and (meth)acrylic esters which more effectively inhibits their polymerization than the existing processes.

We have found that this object is achieved by a process for preparing and/or working up mixtures comprising (meth) acrylic acid and/or (meth)acrylic ester in the presence of at least one polymerization inhibitor and at least one oxygenous gas, which comprises metering in at least part of the oxygenous gas at an exit rate of at least 50 mm/s.

It has been found that bubbles of an oxygenous gas introduced into a (meth)acrylic acid/ester-containing mixture have an average lifetime of up to 5 seconds, in which time oxygen exchange takes place over the geometric surface area of the bubbles. The geometric surface area of the bubbles is substantially determined by the hole diameter, and the lifetime of the bubbles increases with falling hole diameter.

It has also been found that an increased exit rate of the gas improved the exchange of the oxygen with the liquid phase as a consequence of increased convection.

To this end, it is necessary in accordance with the invention that the exit rate of the oxygenous gas from the introducing apparatus is at least 50 mm/s, preferably at least 100 mm/s, more preferably at least 250 mm/s, even more preferably at least 500 mm/s, in particular at least 1000 mm/s and especially at least 5000 mm/s.

At lower exit rates, there is on the one hand the risk that the (meth)acrylic acid/ester-containing mixture rises back into the introducing apparatus, and, on the other hand, that the oxygenous gas only forms an irregular, intermittent stream through the mixture, so that the oxygen exchange is not optimum.

For example, an oxygenous gas can be introduced into a reactor or a reaction zone as follows:

(Meth)acrylic acid is esterified with an alcohol or a (meth)acrylic ester is transesterified with an alcohol generally in one or more reactor(s) which are connected in series and have at least one rectification column and condensers.

The reaction temperature is generally 80–140° C., preferably from 100 to 130° C., and the pressure is from 200 mbar to atmospheric pressure, preferably 300–800 mbar and more preferably from 400 to 600 mbar.

In the case of a plurality of reactors, the temperature in the different reactors may be the same or different, for example they rise or fall in the course of the reactors, preferably rise.

The heat can be introduced via wall heating and/or the external or internal heat exchangers, for example tube or plate heat exchangers, preferably the external circulation evaporators. The rectification columns are of known design and have separating internals (for example bubble-cap, Thormann, valve, sieve or dual-flow trays) or contain random packings or structured packings. The condensers are likewise of known design and can be operated indirectly, for example as tube or plate heat exchangers, or directly, for example as quench coolers. The reaction solution is uniformly mixed in a known manner, for example by stirring, circulation by pumping, forced or natural circulation, preferably by forced or natural circulation.

According to the invention, the reaction zone and/or the heat exchangers, for example the distillation units or reactors installed in the plant is/are purged with an oxygenous gas. This can be effected, for example, as described in EP-A1 1 035 102, column 3, line 41 to column 4, line 16 and also column 4, lines 30 to 51, and also in the examples there. In this process, the oxygenous gas is metered in at at least one point in a pumping circuit between aspiration nozzles, for example at a reactor or the bottom of a column, and a heat exchanger, for example tube bundle or plate heat exchanger, and/or into a heat exchanger, for example, in the case of tube bundle heat exchangers, at at least one point between tube plate and the entrance hood spanning its end. Preferably, an oxygenous gas should be metered in only after any circulation pump present in the circuit, in order to avoid cavitation problems.

Preference is given to passing this oxygenous gas along the heat exchanger surfaces present, more preferably in a forced or natural circulation evaporator present.

To this end, the oxygenous gas is metered with pressure or volume control in a suitable feed apparatus (see below) in the vicinity of the heat exchanger surface present, so that the preferably continuous stream of the oxygenous gas is conducted in countercurrent or cocurrent to the liquid along the heat exchanger surface.

The oxygenous gas can be preheated to the temperature of the heat exchanger medium, so that the temperature of the oxygenous gas differs from the temperature of the heating medium by, for example, not more than 15° C., preferably not more than 10° C.

Based on the volume of the reaction mixture (=1 part by volume) in the reactors and then in any postreactors present in the reaction zone, in each case 0.1–100 parts by volume of oxygenous gas are conducted through heat exchangers, i.e. the reaction zone, per hour, preferably 0.2–80 parts by volume, more preferably 0.5–70 parts by volume and in particular 1–50 parts by volume.

In a particularly preferred manner, the oxygenous gas is passed over the heat exchangers in which the reaction medium is heated in the reactors or in the distillation columns.

(Meth)acrylic acid or (meth)acrylic esters, summarized in this document as (meth)acrylic acid/ester, are generally worked up in at least one column by a distillative or rectificative route or by a fractional condensation.

Mixtures which can be used in accordance with the invention are, for example, those which comprise at least 5% by weight, preferably at least 10% by weight, more preferably at least 25% by weight, even more preferably at least 75% by weight and in particular at least 90% by weight, of acrylic acid or methacrylic acid, referred to in this document as (meth)acrylic acid, or of (meth)acrylic ester. (Meth) acrylic esters may be, for example, methyl, ethyl, n-propyl, isopropyl, n-butyl, sec-butyl, isobutyl, tert-butyl, pentyl, hexyl, octyl, 2-ethylhexyl, dodecyl, 2-hydroxyethyl, 4-hydroxybutyl, 6-hydroxyhexyl, dihydrocyclopentadienyl or 2-dimethylaminoethyl (meth)acrylate and also ethylene glycol, 1,4-butanediol or 1,6-hexanediol di(meth)acrylate, trimethylolpropane triacrylate or pentaerythritol tetraacrylate.

It will be appreciated that this concept can also be applied to other polymerizable compounds, for example styrene, vinyl acetate, vinyl propionate, allylacetic acid, vinylacetic acid or N-vinylformamide.

The mixture comprising (meth)acrylic acid and/or (meth) acrylic ester is generally fed to the column in gaseous form, i.e. as a hot gas mixture, or in liquid form or in a mixed gas-liquid form.

Suitable hot gas mixtures are gas mixtures as obtained as the reaction gas mixture in the catalytic gas phase oxidation of $C_3$-alkanes, -alkenes, -alkanols and/or -alkanals and/or precursors thereof to acrylic acid by known processes. It is particularly advantageous to use propene, propane or acrolein. However, useful starting compounds are also those from which the actual $C_3$-starting compound is formed as a intermediate only during the gas phase oxidation. Acrylic acid can also be prepared directly from propane. When propane is used as the starting material, it can be converted to a propene/propane mixture by known processes of catalytic oxydehydrogenation, homogeneous oxydehydrogenation or catalytic dehydrogenation. Suitable propene/propane mixtures are also refinery propene (approx. 70% of propene and 30% of propane) or cracker propene (approx. 95% of propene and 5% propane). When a propene/propane mixture is used to prepare acrylic acid, propane acts as a diluent gas and/or reactant. When acrylic acid is prepared, the starting gas is generally diluted with gases which are inert under the selected reaction conditions, such as nitrogen ($N_2$), $CO_2$, saturated $C_1$–$C_6$-hydrocarbons and/or steam and passed over transition metal (for example comprising Mo and V, or Mo, W, Bi and Fe) mixed oxide catalysts in a mixture with oxygen ($O_2$) or an oxygenous gas at elevated temperatures (typically from 200 to 450° C.) and also optionally elevated pressure, and oxidatively converted to acrylic acid. These conversions can be carried out in one or more stages.

In addition to the desired acid, the resulting reaction gas mixture comprises secondary components such as unconverted acrolein and/or propene, steam, carbon monoxide, carbon dioxide, nitrogen, oxygen, acetic acid, propionic acid, formaldehyde, further aldehydes and maleic acid or maleic anhydride. Typically, the reaction mixture comprises, based in each case on the entire reaction gas mixture, from 1 to 30% by weight of acrylic acid, from 0.01 to 1% by weight of propene and from 0.05 to 1% by weight of acrolein, from 0.05 to 10% by weight of oxygen, from 0.01 to 3% by weight of acetic acid, from 0.01 to 2% by weight of propionic acid, from 0.05 to 1% by weight of formaldehyde, from 0.05 to 2% by weight of other aldehydes, from 0.01 to 0.5% by weight of maleic acid and maleic anhydride and also small amounts of acetone and the remainder of inert diluent gases. Inert diluent gases present are in particular saturated $C_1$–$C_6$-hydrocarbons such as methane and/or propane, and in addition steam, carbon oxides and nitrogen.

In a similar manner, methacrylic acid can be prepared from $C_4$-alkanes, -alkenes, -alkanols and/or -alkanals and/or precursors thereof, for example from tert-butanol, isobutene, isobutane, isobutyraldehyde, methacrolein, isobutyric acid or methyl tert-butyl ether.

In addition to (meth)acrylic acid, a (meth)acrylic acid-containing mixture can also contain a solvent.

The solvent may have been used in a preceding absorption and/or extraction and comprises the substances known to those skilled in the art for this purpose, for example water, methyl acrylate, ethyl acrylate, butyl acrylate, ethyl acetate, butyl acetate, biphenyl, diphenyl ether, dimethyl ortho-phthalate, diethyl ortho-phthalate, dibutyl ortho-phthalate or mixtures thereof.

Preference is given to using water or a mixture of diphenyl ether and biphenyl, preferably in a weight ratio of from 10:90 to 90:10, or a mixture to which from 0.1 to 25% by weight (based on the total amount of biphenyl and diphenyl ether) of at least one ortho-phthalic ester, for example dimethyl ortho-phthalate, diethyl ortho-phthalate or dibutyl ortho-phthalate, have additionally been added.

When a (meth)acrylic ester-containing mixture is conducted into the column, it can, in addition to (meth)acrylic ester, also comprise (meth)acrylic acid, water, a solvent which forms an azeotrope with water, for example n-pentane, n-hexane, n-heptane, cyclohexane, methylcyclohexane, benzene, toluene or xylene, esterification catalyst, for example sulfuric acid, phosphoric acid, alkylsulfonic acids (e.g. methanesulfonic acid, trifluoromethanesulfonic acid) and arylsulfonic acids (e.g. benzene-, p-toluene- or dodecylbenzenesulfonic acid), transesterification catalyst, for example titanium tetraalkoxide, and natural polymers and oligomers, for example Michael addition products which are formed by addition of alcohols or (meth)acrylic acid to the double bond of (meth)acrylic compounds, for example alkoxypropionic acids or acryloxypropionic acids, and also their esters.

The column into which the (meth)acrylic acid- or (meth) acrylic ester-containing mixture is conducted may be a distillation, rectification or reaction column, or be a column for fractional condensation.

The mixture may optionally have been previously cooled or heated, directly or indirectly, for example by a quench, e.g. spray cooler, Venturi scrubber, bubble columns or other apparatus having sprayed surfaces, or tube bundle or plate heat exchangers.

The column is one of a design known per se having installed separating internals and at least one means of condensation in the top region.

Useful column internals are in principle all common internals, in particular trays, structured packings and/or random packings. Among the trays, preference is given to bubble-cap trays, sieve trays, valve trays, Thormann trays and/or dual-flow trays, and among the random packings, preference is given to those having rings, helices, saddles, Raschig, Intos or Pall rings, barrel or Intalox saddles, Top-Pak, etc., or braids. It will be appreciated that combinations of separating internals are also possible.

Typically, the total number of the theoretical plates in the column is from 5 to 100, preferably from 10 to 80, more preferably from 20 to 80 and most preferably from 50 to 80.

In the case of a column for fractional condensation, the operating pressure in the column is generally from 0.5 to 5 bar (absolute), frequently from 0.5 to 3 bar (absolute) and in many cases from 0.5 to 2 bar (absolute), and in the case of a rectification column, the pressure is generally from 10 mbar to atmospheric pressure, preferably from 20 mbar to atmospheric pressure, more preferably from 20 to 800 mbar and most preferably from 20 to 500 mbar.

According to the invention, the feed of the mixture is not decisive, although it is generally in the lower half of the column, preferably in the lower third.

According to the invention, the reflux at which the column is operated is likewise irrelevant. The reflux may, for example, become 100:1 to 1:100, preferably from 50:1 to 1:50, more preferably from 20:1 to 1:20 and most preferably from 10:1 to 1:10, but may also be zero (no reflux).

According to the invention, the withdrawal point of the product to be purified in the column is not decisive. In general, a column has at least two withdrawal means for product streams, typically one at the top and one at the bottom, and also optionally one or more sidestream takeoffs. For example, the product can be removed overhead or via at least one sidestream takeoff. In the latter case, the withdrawal can be effected in liquid or gaseous form. Preference is given to effecting the withdrawal via a sidestream takeoff.

It is essential to the invention that an oxygenous gas is fed in at a rate of at least 50 mm/s, preferably at least 100 mm/s, more preferably at least 250 mm/s, even more preferably at least 500 mm/s, in particular at least 1000 mm/s and especially at least 5000 mm/s.

The feeding can be effected at at least one point, preferably at a plurality of points.

Preferred oxygenous gases are air or a mixture of air and a gas which is inert under reaction conditions. Useful inert gases include nitrogen, helium, argon, carbon monoxide, carbon dioxide, steam, lower hydrocarbons or mixtures thereof. The oxygen content of the oxygenous gas may, for example, be up to 21% by volume, preferably from 1 to 21% by volume, more preferably from 5 to 21% by volume, and most preferably from 10 to 20% by volume. It will be appreciated that, if desired, higher oxygen contents can also be used.

According to the invention, the amount of oxygenous gas fed in is not limited. It is advantageously from 0.0001 to 100 times the weight of the mixture fed into the column, preferably from 0.0001 to 10 times, more preferably from 0.0005 to 1 time and most preferably from 0.001 to 1 time. It will be appreciated that larger or smaller amounts are also conceivable.

In a preferred embodiment, the oxygenous gas is also metered into the column while the liquid feed into the column is stopped, i.e. the mixture conducted into the column is circulated. In this case, the weight ratio of the amount of the oxygenous gas fed in, based on the mixture conducted into the column, is infinite.

The amount of the oxygenous gas fed in is, for example, from 0.0001 to 10 times the weight of the amount refluxed in the column, preferably from 0.0005 to 1 time, more preferably from 0.0025 to 0.5 time and most preferably from 0.0025 to 0.05 time.

Typically, the gas loading factors of a column are from 1 to 3 $Pa^{0.5}$, preferably from 1.5 to 2.5 $Pa^{0.5}$ and liquid flow rates of from 1 to 50 m/h, preferably 2–10 m/h.

The oxygenous gas can be fed in via any desired apparatus which allows the exit rates of the oxygenous gas according to the invention.

For example, these may be curved or straight inserted or immersed tubes which may optionally be provided with further orifices, nozzles or valves, or apparatus as described in EP-A1 1 035 102, preferably from column 4 lines 30 to 50 and in FIGS. 2 to 6.

Figure 1:
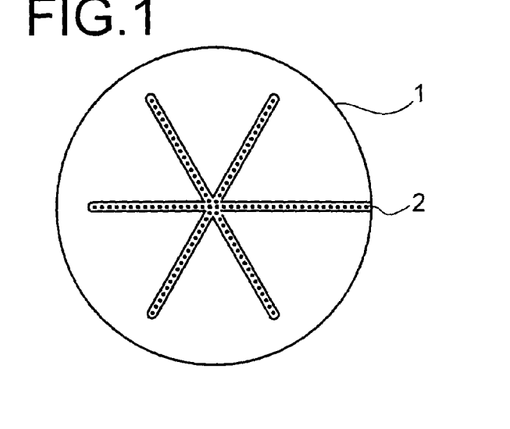
Figure 2A:
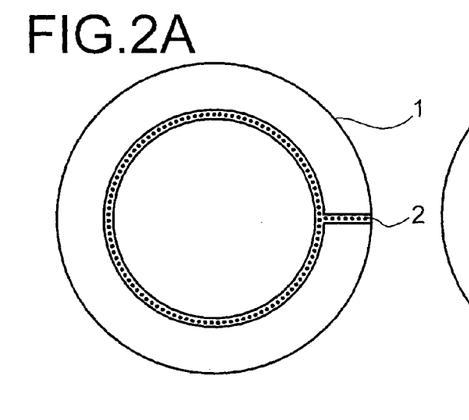
Figure 2B:
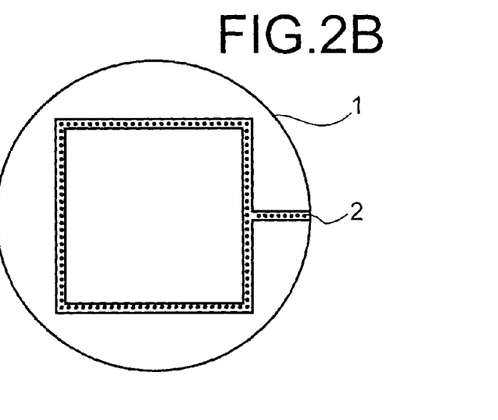
Figure 3:
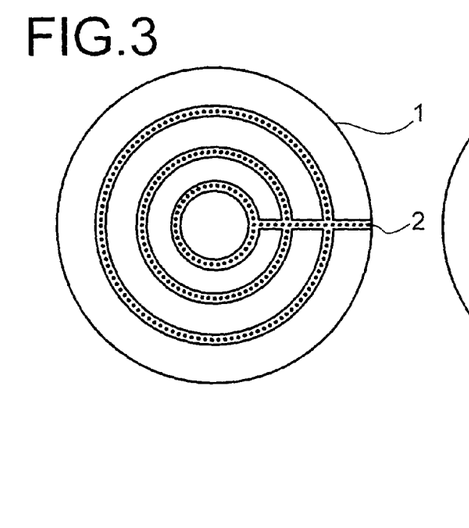
Figure 4:
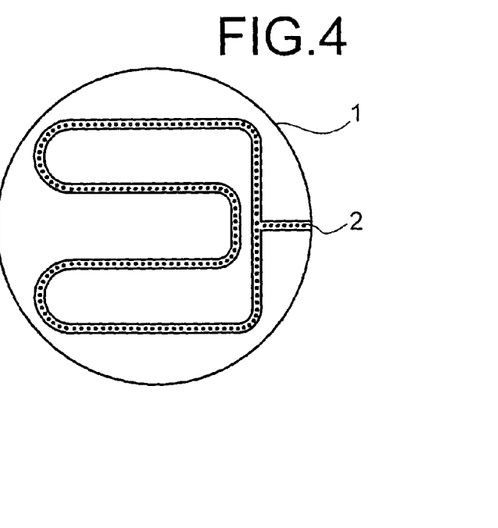
Figure 5:
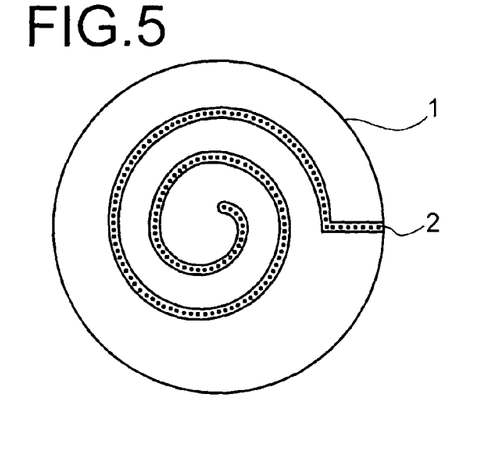
Figure 6:
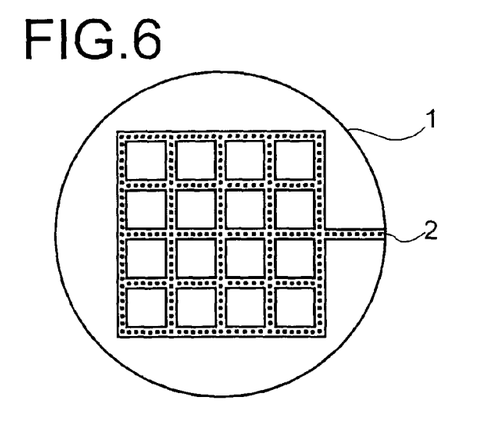
Figure 7:
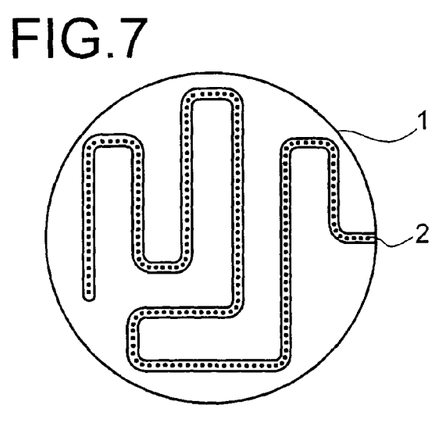
Figure 8:
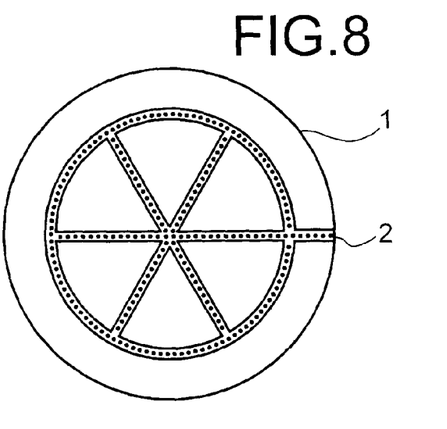

Preference is given to metering apparatus which enables uniform distribution of the oxygenous gas over the surface area of the separating internals (1 in the figures) or of a tube cross section. Preference is given to lines, for example tubes or pipes, which diverge in a star shape from the middle of the surface (FIG. 1) and in whose walls there are orifices through which the oxygenous gas can flow out, one (FIG. 2a) or more (FIG. 3) concentric lines which are circular or bent into another regular shape, for example lines assuming oval or quadrilateral or hexagonal shapes (FIG. 2b), lines laid as loops over the surface (1) (FIG. 4), lines curved into a spiral (FIG. 5), lines arranged in the form of a lattice (FIG. 6) or irregularly, for example as in FIG. 7, or combinations thereof (for example FIG. 8), likewise in each case with appropriate orifices. The lines can be charged with oxygenous gas, for example, via at least one external feed (2 in the figures). Particular preference is given to circular lines.

The internal diameter of the lines should be such that the pressure drop of the oxygenous gas passed through is kept as low as possible, and it should be, for example, between 5 and 100 mm, preferably between 8 and 100 mm, more preferably between 10 and 80, even more preferably from 15 to 70 and in particular from 25 to 70.

The material from which the metering apparatus is manufactured is not decisive to the invention, although it should be stable to corrosion toward the mixture to be separated under the particular conditions. They are preferably manufactured from stainless steel or copper or from copper-plated material, although plastics which are stable under the particular conditions, for example Teflon® or Kevlar® are also conceivable.

The thickness of the material from which the metering apparatus is manufactured should be very low, in order to keep the pressure drop occurring very low, but should of course be sufficient to stabilize the metering apparatus. The wall thickness of the material should, for example, not be more than 5 mm, preferably not more than 4 mm, more preferably from 0.5 to 3 mm and most preferably from 1 to 2 mm.

The orifices in the devices may be, for example, holes, slots, valves or nozzles, preferably holes of any desired shape, preferably round holes. The orifices may be distributed at any desired point over the metering apparatus, for example on the upper side and/or lower side and/or on the walls and/or randomly over the surface of the metering apparatus, preferably on the lower half, more preferably on the lower side.

In order to make possible the above-listed gas introduction rates, the orifices in the apparatus in the case of an appropriate gas stream should, for example, have a surface area of up to 0.8 $cm^2$ (corresponding to a round hole of diameter about 1 cm), preferably up to 0.5 $cm^2$, more preferably up to 0.3 $cm^2$, even more preferably up to 0.2 $cm^2$, in particular up to 0.1 $cm^2$ and especially up to 0.05 $cm^2$.

In order to counteract the back pressure occurring and the pressure drops therefore occurring along the flow direction, the orifice cross sections can also be changed along the passage direction through the lines, for example increase along the flow direction, in order to ensure uniform flow out of the orifices.

The number of metering apparatus in the column is dependent upon the type and number of the separating internals. A minimum of at least one apparatus is installed in the column. The upper limit should essentially be one metering apparatus for a practical separating tray, or, in the case of structured packings, one metering apparatus for a structured packing. Preference is given to from 1 to 20, more preferably from 2 to 15, even more preferably from 5 to 15 and in particular from 7 to 13, metering apparatus for metering in an oxygenous gas. These are preferably disposed in the upper section of the column, the upper section of the column referring to the upper 75% of the column, based on the theoretical plates, preferably the upper 50%, more preferably the upper 40%, even more preferably the upper 33% and in particular the upper 25%. In a preferred embodiment, feeding is effected up to 2 theoretical plates below any sidestream takeoff present, more preferably up to 2 theoretical plates below the uppermost sidestream takeoff.

The metering apparatus may be mounted at any desired points in the course of the preparation and/or purification process, preferably at points at which the oxygenous gas can be introduced into a liquid phase or liquid/gaseous interface layer, for example froth layers in rectification columns. The introduction into a liquid phase can be effected, for example, into a standing or moving liquid in a reactor, a receiver, intermediate or storage vessel, a condensate vessel or into a circulate (see above), for example of a reactor or of a distillation or rectification column, preferably as described in EP-A1 1 035 102, column 3 line 41 to column 4 line 16 and column 4 lines 30 to 51, and also in the examples.

The metering in according to the invention of an oxygenous gas generally attains an oxygen content in the liquid phase of at least 0.1 ppm, preferably at least 0.2 ppm, more preferably 0.3 ppm, even more preferably 0.4 ppm and in particular at least 0.5 ppm.

Typically, the mixture to be separated in the column or disposed in the reactor is stabilized against polymerization using at least one stabilizer. This at least one stabilizer can be conducted into the column with the mixture and/or be additionally introduced into the column during the separation, for example with a reflux stream.

Examples of useful stabilizers include phenolic compounds, amines, nitro compounds, phosphorus or sulfur compounds, hydroxylamines, N-oxyls and certain inorganic salts, and also optionally mixtures thereof.

Preference is given to stabilizers such as phenothiazine, N-oxyls and phenolic compounds.

Examples of N-oxyls (nitroxyl or N-oxyl radicals, i.e. compounds containing at least one >N—O. group) include 4-hydroxy-2,2,6,6-tetramethylpiperidine N-oxyl, 4-oxo-2,2,6,6-tetramethylpiperidine N-oxyl, 4-acetoxy-2,2,6,6-tetramethylpiperidine N-oxyl, 2,2,6,6-tetramethylpiperidine N-oxyl or 3-oxo-2,2,5,5-tetramethylpyrrolidine N-oxyl.

Examples of phenolic compounds include alkylphenols, for example o-, m- or p-cresol (methylphenol), 2-tert-butyl-4-methylphenol, 6-tert-butyl-2,4-dimethylphenol, 2,6-di-tert-butyl-4-methyl-phenol, 2-tert-butylphenol, 4-tert-butylphenol, 2,4-di-tert-butylphenol, 2-methyl-4-tert-butylphenol, 4-tert-butyl-2,6-dimethylphenol or 2,2'-methylenebis(6-tert-butyl-4-methyl-phenol), 4,4'-oxydiphenol, 3,4-methylenedioxydiphenol (sesamol), 3,4-dimethylphenol, hydroquinone, pyrocatechol (1,2-dihydroxybenzene), 2-(1'-methylcyclohex-1'-yl)-4,6-dimethylphenol, 2- or 4-(1'-phenyleth-1'-yl)phenol, 2-tert-butyl-6-methylphenol, 2,4,6-tris-tert-butylphenol, 2,6-di-tert-butylphenol, 2,4-di-tert-butylphenol, 4-tert-butylphenol, nonylphenol [11066-49-2], octylphenol [140-66-9], 2,6-dimethylphenol, bisphenol A, bisphenol F, bisphenol B, bisphenol C, bisphenol S, 3,3',5,5'-tetrabromobisphenol A, 2,6-di-tert-butyl-p-cresol, Koresin® from BASF AG, methyl 3,5-di-tert-butyl-4-hydroxybenzoate, 4-tert-butylpyrocatechol, 2-hydroxybenzyl alcohol, 2-methoxy-4-methylphenol, 2,3,6-trimethylphenol, 2,4,5-trimethylphenol, 2,4,6-trimethylphenol, 2-isopropylphenol, 4-isopropylphenol, 6-isopropyl-m-cresol, n-octadecyl β-(3,5-di-tert-butyl-4-hydroxyphenyl)propionate, 1,1,3-tris(2-methyl-4-hydroxy-5-tert-butylphenyl)butane, 1,3,5-trimethyl-2,4,6-tris(3,5-di-tert-butyl-4-hydroxybenzyl)-benzene, 1,3,5-tris (3,5-di-tert-butyl-4-hydroxybenzyl) isocyanurate, 1,3,5-tris (3,5-di-tert-butyl-4-hydroxyphenyl)propionyloxyethyl isocyanurate, 1,3,5-tris(2,6-dimethyl-3-hydroxy-4-tert-butylbenzyl) isocyanurate or pentaerythrityl tetrakis[β-(3,5-di-tert-butyl-4-hydroxyphenyl)propionate], 2,6-di-tert-butyl-4-dimethylaminomethylphenol, 6-sec-butyl-2,4-dinitrophenol, Irganox® 565, 1141, 1192, 1222 and 1425 from Ciba Spezialitätenchemie, octadecyl 3-(3',5'-di-tert-butyl-4'-hydroxyphenyl)propionate, hexadecyl 3-(3',5'-di-tert-butyl-4'-hydroxyphenyl)propionate, octyl 3-(3',5'-di-tert-butyl-4'-hydroxyphenyl)propionate, 3-thia-1,5-pentanediol bis[(3',5'-di-tert-butyl-4'-hydroxyphenyl) propionate], 4,8-dioxa-1,11-undecanediol bis[(3',5'-di-tert-butyl-4'-hydroxyphenyl)propionate], 4,8-dioxa-1,11-undecanediol bis[(3'-tert-butyl-4'-hydroxy-5'-methylphenyl) propionate], 1,9-nonanediol bis[(3',5'-di-tert-butyl-4'-hydroxyphenyl)propionate], 1,7-heptanediaminebis[3-(3',5'-di-tert-butyl-4'-hydroxyphenyl)-propionamide], 1,1-methanediaminebis[3-(3',5'-di-tert-butyl-4'-hydroxyphenyl)-propionamide], 3-(3',5'-di-tert-butyl-4'-hydroxyphenyl)propionic hydrazide, 3-(3',5'-dimethyl-4'-hydroxyphenyl)propionic hydrazide, bis(3-tert-butyl-5-ethyl-2-hydroxyphen-1-yl)methane, bis(3,5-di-tert-butyl-4-hydroxyphen-1-yl)methane, bis[3-(1'-methylcyclohex-1'-yl)-5-methyl-2-hydroxyphen-1-yl]-methane, bis(3-tert-butyl-2-hydroxy-5-methylphen-1-yl)methane, 1,1-bis(5-tert-butyl-4-hydroxy-2-methylphen-1-yl)ethane, bis(5-tert-butyl-4-hydroxy-2-methylphen-1-yl)sulfide, bis(3-tert-butyl-2-hydroxy-5-methylphen-1-yl)sulfide, 1,1-bis(3,4-dimethyl-2-hydroxyphen-1-yl)-2-methylpropane, 1,1-bis(5-tert-butyl-3-methyl-2-hydroxyphen-1-yl)butane, 1,3,5-tris [1'-(3",5"-di-tert-butyl-4"-hydroxyphen-1"'-yl)-meth-1'-yl]-2,4,6-trimethylbenzene, 1,1,4-tris(5'-tert-butyl-4'-hydroxy-2'-methylphen-1'-yl)butane, aminophenols such as para-aminophenol, nitrosophenols such as para-nitrosophenol, p-nitroso-o-cresol, alkoxyphenols, for example 2-methoxyphenol(guaiacol, pyrocatechol monomethyl ether), 2-ethoxyphenol, 2-isopropoxyphenol, 4-methoxyphenol (hydroquinone monomethyl ether), mono- or di-tert-butyl-4-methoxyphenol, 3,5-di-tert-butyl-4-hydroxyanisole, 3-hydroxy-4-methoxybenzyl alcohol, 2,5-dimethoxy-4-hydroxybenzyl alcohol (syringa alcohol), 4-hydroxy-3-methoxybenzaldehyde (vanillin), 4-hydroxy-3-ethoxybenzaldehyde (ethylvanillin), 3-hydroxy-4-methoxybenzaldehyde (isovanillin), 1-(4-hydroxy-3-methoxyphenyl)ethanone (acetovanillone), eugenol, dihydroeugenol, isoeugenol, tocopherols such as α-, β-, γ-, δ- and ε-tocopherol, tocol, α-tocopherolhydroquinone and also 2,3-dihydro-2,2-dimethyl-7-hydroxybenzofuran (2,2-dimethyl-7-hydroxycoumarin), quinones and hydroquinones such as hydroquinone, 2,5-di-tert-butylhydroquinone, 2-methyl-p-hydroquinone, 2,3-dimethylhydroquinone, trimethylhydroquinone, 4-methylpyrocatechol, tert-butylhydroquinone, 3-methylpyrocatechol, benzoquinone, 2-methyl-p-hydroquinone, 2,3-dimethylhydroquinone, trimethylhydroquinone, 3-methylpyrocatechol, 4-methylpyrocatechol, tert-butylhydroquinone, 4-ethoxyphenol, 4-butoxyphenol, hydroquinone monobenzyl ether, p-phenoxyphenol, 2-methylhydroquinone, 2,5-di-tert-butylhydroquinone, tetramethyl-p-benzoquinone, diethyl 1,4-cyclohexanedione-2,5-dicarboxylate, phenyl-p-benzoquinone, 2,5-dimethyl-3-benzyl-p-benzoquinone, 2-isopropyl-5-methyl-p-benzoquinone (thymoquinone), 2,6-diisopropyl-p-benzoquinone, 2,5-dimethyl-3-hydroxy-p-benzoquinone, 2,5-dihydroxy-p-benzoquinone, embelin, tetrahydroxy-p-benzoquinone, 2,5-dimethoxy-1,4-benzoquinone, 2-amino-5-methyl-p-benzoquinone, 2,5-bisphenylamino-1,4-benzoquinone, 5,8-dihydroxy-1,4-naphthoquinone, 2-anilino-1,4-naphthoquinone, anthraquinone, N,N-dimethylindoaniline, N,N-diphenyl-p-benzoquinone diimine, 1,4-benzoquinone dioxime, coerulignone, 3,3'-di-tert-butyl-5,5'-dimethyldiphenoquinone, p-rosolic acid (aurin), 2,6-di-tert-butyl-4-benzylidenebenzoquinone or 2,5-di-tert-amylhydroquinone.

Aromatic amines are, for example, N,N-diphenylamine; phenylenediamines are, for example, N,N'-dialkyl-para-phenylenediamine, where the alkyl radicals may each independently contain from 1 to 4 carbon atoms and may be linear or branched; hydroxylamines are, for example, N,N-diethylhydroxylamine; phosphorus compounds are, for example, triphenylphosphine, triphenyl phosphite or triethyl phosphite, sulfur compounds are, for example, diphenyl sulfide and inorganic salts are, for example, the chloride, dithiocarbamate, sulfate, salicylate and acetate salts of copper, manganese, cerium, nickel and chromium.

Preference is given to phenothiazine, p-aminophenol, p-nitrosophenol, 2-tert-butylphenol, 4-tert-butylphenol, 2,4-di-tert-butylphenol, 2-methyl-4-tert-butylphenol, 4-tert-butyl-2,6-dimethylphenol, hydroquinone and/or hydroquinone monomethyl ether, and also manganese(II) acetate, cerium (III) carbonate or cerium(III) acetate; particular preference is given to phenothiazine, p-aminophenol, p-nitrosophenol, 2-tert-butylphenol, 4-tert-butylphenol, 2,4-di-tert-butylphenol, 2-methyl-4-tert-butylphenol, 4-tert-butyl-2,6-dimethylphenol, hydroquinone and/or hydroquinone monomethyl ether.

Very particular preference is given to phenothiazine, hydroquinone monomethyl ether and a mixture of hydroquinone monomethyl ether and phenothiazine.

The way in which the stabilizer is added is not limited. The stabilizer added may in each case be added individually or as a mixture, in liquid form or in dissolved form in a suitable solvent which may itself be a stabilizer, as described, for example, in DE-A 102 00 583.

The stabilizer may, for example, be added in a suitable formulation at any desired point in the column, to an external cooling circuit or to a suitable recycle stream. Preference is given to adding directly into the column or into a recycle stream.

When a mixture of a plurality of stabilizers is used, these may be fed independently at different metering points or at the same metering points as those mentioned above.

When a mixture of a plurality of stabilizers is used, these may also be dissolved independently in different solvents.

Depending on the individual substance, the concentration of the stabilizer in the column may be between 1 and 10 000 ppm, preferably between 10 and 5000 ppm, more preferably between 30 and 2500 ppm and in particular between 50 and 1500 ppm.

Particular preference is given to spraying the dissolved stabilizer (mixture) onto any condenser surfaces, column internals or column lids present.

The product removed from the column, i.e. (meth)acrylic acid or (meth)acrylic ester, may have any desired purities which are not essential to the invention, for example at least 90%, preferably at least 95%, more preferably at least 98% and most preferably at least 99%.

In the case of crude acrylic acid which may, for example, be removed in a sidestream takeoff, the following may generally be present in addition to acrylic acid:

| from 0.1 to 2% by weight | of lower carboxylic acids, for example acetic acid, propionic acid |
| from 0.5 to 5% by weight | of water |
| from 0.05 to 1% by weight | of low molecular weight aldehydes, e.g. benzaldehyde, 2- or 3-furfural, acrolein |
| from 0.01 to 1% by weight | of maleic acid and/or its anhydride |
| from 1 to 500 ppm by weight | of stabilizer, | based in each case on the weight of the crude acrylic acid.

Glacial acrylic acid purified in the column may, for example, have the following composition:

| acrylic acid | 99.7–99.9% by weight |
| acetic acid | 50–1500 ppm by weight |
| propionic acid | 10–500 ppm by weight |
| diacrylic acid | 10–1000 ppm by weight |
| water | 50–1000 ppm by weight |
| aldehyde and other carbonylics | 1–50 ppm by weight |
| inhibitors | 100–300 ppm by weight |
| maleic acid/anhydride | 1–20 ppm by weight |

The process according to the invention for working up (meth)acrylic acid or (meth)acrylic esters is preferably part of an overall process for preparing (meth)acrylic acid or (meth)acrylic esters which, in a preferred embodiment for acrylic acid, comprises the following steps:

(a) catalytic gas phase oxidation of propane, propene and/or acrolein to acrylic acid to obtain a gaseous reaction product containing acrylic acid, (b) absorption of the reaction product with a solvent, (c) distillation of the solvent laden with reaction product to obtain crude acrylic acid and the solvent, (d) optionally purifying the crude acrylic acid by crystallization and (e) optionally esterifying the crude or crystallized acrylic acid.

Stage a

According to the invention, the $C_3$ starting compounds may be catalytically reacted in the gas phase with molecular oxygen to give acrylic acid by known processes as described above.

The conversion of propene to acrylic acid is strongly exothermic. The reaction gas which, in addition to the reactants and products, advantageously comprises a diluent gas, for example cycle gas, nitrogen from air and/or steam, can therefore only take up a small portion of the heat of reaction. Although the type of reactors used is subject to no restriction per se, tube bundle heat exchangers are usually used which are charged with oxidation catalyst, since they are capable of removing the predominant portion of the heat released in the reaction by convection and radiation at the cooled tube walls.

However, stage (a) does not provide pure acrylic acid, but rather a gaseous mixture which, in addition to acrylic acid, comprises secondary components which are substantially unconverted acrolein and/or propene, steam, carbon monoxide, carbon dioxide, nitrogen, oxygen, acetic acid, propionic acid, formaldehyde, further aldehydes and maleic anhydride.

Typically, the reaction product mixture, based in each case on the entire reaction mixture, comprises from 0.05 to 1% by weight of propene and from 0.05 to 1% by weight of acrolein, from 0.01 to 2% by weight of propane, from 1 to 20% by weight of steam, from 0.05 to 15% by weight of carbon oxides, from 10 to 90% by weight of nitrogen, from 0.05 to 5% by weight of oxygen, from 0.05 to 2% by weight of acetic acid, from 0.01 to 2% by weight of propionic acid, from 0.05 to 1% by weight of formaldehyde, from 0.05 to 2% by weight of aldehydes and also from 0.01 to 0.5% by weight of maleic anhydride.

Stage b

In stage (b), the acrylic acid and a portion of the secondary components from the reaction gas is removed by absorption with a solvent. According to the invention, useful solvents are water or especially all high-boiling solvents, preferably solvents having a boiling point above 160° C. A particularly suitable solvent is a mixture of diphenyl ether and biphenyl, especially the commercially obtainable mixture of 75% by weight of diphenyl ether and 25% by weight of biphenyl, to which, as mentioned above, ortho-phthalic ester may be added.

In the present context, the terms high boilers, medium boilers and low boilers and also corresponding terms used as adjectives refer to compounds which have a higher boiling point than acrylic acid (high boilers), those which have approximately the same boiling point as acrylic acid (medium boilers), and those which have a lower boiling point than acrylic acid (low boilers).

Advantageously, the hot reaction gas obtained from stage (a) is cooled before the absorption by partially evaporating the solvent in a suitable apparatus, for example a direct condenser or quench apparatus. Useful apparatus for this purpose include Venturi scrubbers, bubble columns and spray condensers.

The high-boiling secondary components of the reaction gas from stage (a) condense into the unevaporated solvent. The partial evaporation of the solvent is also a purification step for the solvent. In a preferred embodiment of the invention, a substream of the unevaporated solvent, preferably from 1 to 10% of the mass stream fed to the absorption column is removed and subjected to solvent purification. In this purification, the solvent is distilled over and the high-boiling secondary components which remain behind may be disposed of, for example incinerated, if required in more highly concentrated form. This solvent distillation serves to avoid too high a concentration of high boilers in the solvent stream.

The absorption is effected in a countercurrent absorption column which is preferably equipped with valve and/or dual-flow trays and is charged from above with (unevaporated) solvent. The gaseous reaction product and any evaporated solvent are passed from below into the column and then cooled to absorption temperature. The cooling is advantageously effected by cooling circuits, i.e. preheated solvent is removed from the column, cooled in heat exchangers and fed back to the column at a point above the takeoff point. In addition to acrylic acid, these solvent cooling circuits also condense low-, high- and medium-boiling secondary components and also evaporated solvent. As soon as the reaction gas stream is cooled to the absorption temperature, the actual absorption is effected. The remainder of the acrylic acid in the reaction gas is absorbed, as is a portion of the low-boiling secondary components.

The remaining, unabsorbed reaction gas from stage (a) is cooled further, in order to remove the condensable portion of the low-boiling secondary components thereof, in particular water, formaldehyde and acetic acid, by condensation. This condensate is referred to hereinbelow as acid water. The remaining gas stream, referred to hereinbelow as cycle gas, consists predominantly of nitrogen, carbon oxides and unconverted reactants. Preference is given to feeding some of this gas stream back to the reaction stages as diluent gas.

A solvent stream laden with acrylic acid, high- and medium-boiling secondary components and also a small portion of low-boiling secondary components is removed from the bottom of the column used in stage (b) and, in a preferred configuration of the invention, subjected to a desorption. This is advantageously carried out in a column which may preferably be equipped with valve and/or dual-flow trays but also with random packings or structured packings, in the presence of what is known as a stripping gas. The stripping gas used may be any inert gas or gas mixture, although preference is given to using a gas mixture of air and nitrogen or cycle gas, since this occurs in stage (a) when carrying out an evaporation of a portion of the solvent. The desorption strips the majority of the low boilers out of the laden solvent using a portion of the cycle gas which is removed before stage (a). Since relatively large amounts of acrylic acid are also stripped, this stream, referred to hereinbelow as stripping cycle gas, is for economic reasons advantageously not discarded, but instead recirculated, for example to the stage at which the solvent is partially evaporated or into the absorption column. Since the stripping gas is part of the cycle gas, it still contains significant amounts of low boilers itself. The performance of the column used for desorption can be increased when the low boilers are removed from the stripping gas before it is passed into the column. In terms of process engineering, this is advantageously carried out in such a way that the stripping gas is purified using solvent worked up in stage (c) described below in a countercurrent scrubbing column.

A virtually low boiler-free, acrylic acid-laden solvent stream may then be removed from the bottom of the column used for the desorption.

Stage c

In process stage (c), the acrylic acid together with the medium-boiling components and also the last residue of low-boiling secondary components are removed from the solvent. This separation is effected by means of distillation, in principle using any distillation column. Preference is given to using a column having sieve trays, for example dual-flow trays, valve trays or crossflow sieve trays made of metal. In the rectifying section of the column, the acrylic acid is distilled to free it of solvent and the medium-boiling secondary components such as maleic anhydride. In order to reduce the proportion of low boilers in the acrylic acid, the rectifying section of the column is advantageously lengthened and the acrylic acid is removed from the column as a sidestream takeoff. This acrylic acid is referred to hereinbelow, irrespective of its purity, as crude acrylic acid.

At the top of the column, a low boiler-rich stream is then removed after a partial condensation. However, since this stream still contains acrylic acid, it is advantageously not discarded, but instead recycled to the absorption stage (b).

The low boiler-free and virtually acrylic acid-free solvent is removed from the bottom of the column, and the majority thereof is preferably fed to the countercurrent scrubbing column in which the stripping gas of stage (b) is purified, in order to scrub the low boilers out of the stripping gas. The virtually acrylic acid-free solvent is then fed to the absorption column.

According to the invention, this column, as described above, is provided with at least one means of metering oxygen-containing gases in the upper section of the column.

It will be appreciated that all apparatus, especially the columns in which an acrylic acid-containing stream is purified, are operated in the manner according to the invention by metering in an oxygenous gas in its upper section.

In a preferred embodiment of the invention, the acid water which may still contain dissolved acrylic acid is treated extractively with a small substream of the virtually acrylic acid-free solvent. This acid water extraction extracts a portion of the acrylic acid in the solvent and thus recovers it from the acid water. At the same time, the acid water extracts the polar medium-boiling components from the solvent stream and thus avoids an increase in these components in the solvent circuit. The acid water stream composed of low and middle boilers may be further concentrated.

The crude acrylic acid obtained in stage (c), based in each case on the crude acrylic acid, preferably comprises from 98 to 99.8% by weight, in particular from 98.5 to 99.5% by weight, of acrylic acid, and from 0.2 to 2% by weight, in particular from 0.5 to 1.5% by weight, of impurities, for example acetic acid, aldehydes and maleic anhydride. This acrylic acid may, as long as the requirements of its purity are not too high, optionally be used directly for esterification.

Stage (d):

In stage (d), the crude acrylic acid obtained in step (c) may be further purified by distillation or crystallization, preferably by means of fractional crystallization by a combination of dynamic and static crystallization. The type of distillation or crystallization here is subject to no particular restriction.

In the static crystallization (for example U.S. Pat. No. 3,597,164 and FR 2 668 946), the liquid phase is moved only by free convection, while in the dynamic crystallization, the liquid phase is moved by forced convection. The latter may be effected by forced flow in apparatus having full flow-through (cf. DE 26 06 364) or by applying a sprayed film or falling film to a cooled wall (DT 1 769 123 and EP 218 545).

Stage (e):

If desired, the crude or glacial acrylic acid obtained in stage (c) or (d) may be esterified by known methods.

To this end, the esterification methods known from the prior art may be used, for example as described in DE-A 101 44 490, EP-A 733 617, EP-A 1 081 125, DE-A 196 04 267 or DE-A 196 04 253. In the course of the preparation and/or workup of the ester, an oxygenous gas may be metered in in accordance with the invention in the upper section of one or more columns, preferably in the column in which the ester is purified by distillation.

The present invention further provides a separating apparatus comprising a column for distillation, rectification and/or fractional condensation, having separating internals, at least one condenser at the top of the column and at least two withdrawal means for product streams, and also comprising at least one gas metering means connected to at least one external feed (2) in the upper section of the column which may be arranged in a star shape, ring shape or another regular shape, comprise a plurality of concentric rings, or be arranged in a coil shape, spiral shape, lattice shape or irregularly.

For the column, the separating internals, the withdrawal means and the gas metering means, the same applies as was said above.

Preference is given to a separating apparatus according to the invention which has at least one ring-shaped or concentric ring-shaped gas metering means, more preferably ring-shaped.

The number of gas metering means, the material, orifices and their positioning in the upper section of the column has already been described above.

The present invention further provides the use of such separating apparatus in the preparation and/or workup of polymerizable compounds, for example styrene, vinyl acetate, vinyl propionate, allylacetic acid, vinylacetic acid, N-vinylformamide, preferably of (meth)acrylic acid and (meth)acrylic esters.

The present invention enables the workup of polymerizable compounds with a reduced degree of polymer formation.

ppm and percentages relate, unless otherwise stated, to percentages by weight and ppm by weight.

EXAMPLES

Example 1

In a rectification column having diameter 3.8 m and length 32 m, a mixture of diphyl/dimethyl phthalate and acrylic acid was distillatively separated. The feed to the column consisted of 17% by weight of acrylic acid
    0.02% by weight of water
    0.0015% by weight of acrolein
    0.0015% by weight of allyl acrylate
    0.01% by weight of furfural
    0.027% by weight of acetic acid
    0.2% by weight of benzaldehyde
    0.003% by weight of propionic acid
    0.032% by weight of maleic anhydride
    58% by weight of diphyl(diphenyl ether/biphenyl)
    17.0% by weight of dimethyl phthalate
    3% by weight of acryloylpropionic acid The mixture was separated in the rectification column in 99.6% acrylic acid, a low boiler mixture comprising 96% of acrylic acid and a high boiler mixture comprising less than 0.5% of acrylic acid. The separating internals used were 46 dual-flow trays. The tray separation was 400 mm. The feed was to tray 8, and 99.6% acrylic acid was removed from tray 40. The temperature at the top of the column was 80° C., the pressure was 105 mbar and the reflux ratio was 1.3. The temperature at the bottom of the column was 193° C. and the pressure was 230 mbar. The reflux of the column was stabilized with phenothiazine in such a way that the product which was removed from the column in the sidestream takeoff contains 250 ppm of phenothiazine. In addition, 200 000 l/h of air were introduced into the lower section of the rectification column for stabilization.

At each of trays 30 to 39, ring-shaped lines were installed. Each ring-shaped line had a diameter of 25 mm, and the underside was disclosed 50 mm above the dual-flow tray and had 200 holes each having a diameter of 5 mm. 40 000 l/h of air were introduced in via each ring-shaped line. The holes were on the underside of the ring-shaped line, i.e. the air was bubbled in downward in a perpendicular direction.

The exit rate of the air from the ring-shaped lines was 2800 mm/s.

At a running time of 40 days, trays 30 to 39 were polymer-free.

Comparative Example 1

The procedure of example 1 was carried out and the air feed via the ring-shaped lines stopped. Instead, the air feed into the lower section of the rectification column was increased to 600 000 l/h.

After a running time of 30 days, the rectification column contained a total of approx. 300 kg of polymer in the region of trays 30 to 39.

Examples 2 to 4

A 500 ml four-neck flask equipped with coil condenser, gas inlet pipe and thermal element was initially charged with 300 g of 99.6% acrylic acid. The acrylic acid used was stabilized at 275 ppm of phenothiazine. In addition, 16 l/h of nitrogen and 70 ml/h of air were passed separately through the initially charged acrylic acid. The initially charged acrylic acid was maintained at a temperature of 25° C. for 2 hours, and the four-necked flask was subsequently immersed in a heating bath preheated to 80° C. and the time to the occurrence of cloudiness was determined as an indication of polymerization.

| Example | Hole diameter | Exit rate | Cloudiness after |
|---|---|---|---|
| 2 | 2 mm | 148.7 cm/s | 58 min |
| 3 | 1 mm | 565 cm/s | 88 min |
| 4 | 0.1 mm | 56.455 cm/s | 101 min |

We claim:

1. A process for enhancing the inhibition of polymerization of a mixture comprising (meth)acrylic acid and/or (meth)acrylic ester and at least one polymerization inhibitor, comprising metering into the mixture at least one oxygenous gas at an exit rate of at least 50 mm/s, wherein the oxygenous gas is metered into the mixture by a metering apparatus, wherein the metering apparatus has orifices with a surface area of up to 0.8 cm$^2$.

2. A process as claimed in claim 1, wherein the oxygenous gas is metered in inserted or immersed tubes which may optionally be provided with further orifices, nozzles, valves or at least one line arranged in a star shape, a ring shape, a plurality of concentric rings, a loop shape, a spiral shape, a lattice shape, regularly or irregularly.

3. A process as claimed in claim 1, wherein the oxygenous gas is metered in at least one point in a pumping circuit between aspirating nozzle and a heat exchanger.

4. A process as claimed in claim 1, wherein the oxygenous gas is metered into a heat exchanger in a pumping circuit.

5. A process as claimed in claim 1, wherein the oxygenous gas is metered into a column for distillation, rectification and/or fractionating condensation.

6. A process as claimed in claim 1, wherein the oxygenous gas is metered into the mixture by a metering device having a wall thickness of not more than 5 mm.

7. A process as claimed in claim 1, wherein the oxygenous gas is metered into a liquid phase and/or a liquid/gaseous interface layer.

8. A process as claimed in claim 1, wherein the oxygenous gas is air or an air/nitrogen mixture.

9. A process as claimed claim 1, wherein the mixture contains acrylic acid.

10. A process as claimed in claim 1, wherein the exit rate is at least 100 mm/s.

11. A process as claimed in claim 1, wherein the exit rate is at least 250 mm/s.

12. A process as claimed in claim 1, wherein the exit rate is at least 500 mm/s.

13. A process as claimed in claim 1, wherein the exit rate is at least 1000 mm/s.

14. A process as claimed in claim 1, wherein the exit rate is at least 5000 mm/s.

15. A process as claimed in claim 1, wherein bubbles of the oxygenous gas have an average lifetime of up to 5 seconds.

16. A process as claimed in claim 1, which is conducted in a column.

17. A process as claimed in claim 16, wherein the total number of theoretical plates in the column is from 5 to 100.

18. A process as claimed in claim 16, wherein the reflux at which the column is operated is 100:1 to 1:100.

19. A process as claimed in claim 1, wherein the oxygenous gas is fed into the mixture at a plurality of points.

* * * * *